United States Patent [19]

Aslam et al.

[11] Patent Number: 5,225,603
[45] Date of Patent: Jul. 6, 1993

[54] PREPARATION OF 4-(6'-METHOXY-2'-NAPHTHYL)-3-BUTEN-2-ONE

[75] Inventors: Mohammad Aslam; Varadaraj Elango, both of Corpus Christi, Tex.

[73] Assignee: Hoechst Celanese Corporation, Somerville, N.J.

[21] Appl. No.: 211,106

[22] Filed: Jun. 17, 1988

Related U.S. Application Data

[63] Continuation of Ser. No. 73,031, Jul. 14, 1987, abandoned.

[51] Int. Cl.$^5$ .............................................. C07C 45/45
[52] U.S. Cl. ..................................... 568/315; 568/318
[58] Field of Search ...................... 568/315, 316, 318

[56] References Cited

U.S. PATENT DOCUMENTS 4,061,779  12/1977  Lake et al. ........................ 568/313
4,221,741  9/1980   Gaster ............................... 568/314

OTHER PUBLICATIONS

Cacchi et al, J. Org. Chem, vol. 48, pp. 4236–4240 (1983).
Heck, Pure & Applied Chem, vol. 50, pp. 691–701 (1978).
Melpolder et al, J. Org. Chem., vol. 41, pp. 265–272 (1976).
Chalk et al, J. Org. Chem, vol. 41, pp. 273–278 (1976).
Chalk et al, J. Org. Chem, vol. 41, pp. 1206–1209 (1976).
Cacchi et al, Synthesis, #7, pp. 575–577 (1984).

*Primary Examiner*—James H. Reamer
*Attorney, Agent, or Firm*—Donald R. Cassady

[57] ABSTRACT

An intermediate for the manufacture of nabumetone, 4-(6'-methoxy-2'-naphthyl)-3-buten-2-one, is prepared by contacting 2-bromo-6-methoxynaphphalene with methyl vinyl ketone in the presence of a palladium catalyst at from about 50° C. to about 200° C. for a time sufficient to cause substantially complete reaction to occur.

8 Claims, No Drawings

PREPARATION OF 4-(6'-METHOXY-2'-NAPHTHYL)-3-BUTEN-2-ONE

This is a continuation of co-pending application Ser. No. 07/073,031 filed on Jul. 14, 1987, now abandoned.

BACKGROUND OF THE INVENTION

The compound 4-(6'-methoxy-2'-naphthyl)-3-buten-2-one is a valuable intermediate in the manufacture of the nonsteroidal anti-inflammatory known as nabumetone. The compound and prior art methods of its manufacture have been described in U.S. Pat. Nos. 4,061,779; 4,221,741; and 4,420,639 assigned to the Beecham Group Limited.

These prior art processes involve (i) the synthesis of 6-methoxy-2-naphthaldehyde by a Grignard reaction of 2-bromo-6-methoxynaphthalene with N,N-dimethylformamide; the base catalyzed aldol condensation of the aldehyde with acetone to form 4-(6'-methoxy-2'-naphthyl)-3-buten-2-one and the subsequent catalytic hydrogenation of that compound using 10% palladium on carbon; or, (ii) the condensation of 6'-methoxy-2'-acetonaphthone with ethyl acetate using sodium hydride in dimethyl sulfoxide and the subsequent hydrogenation of that compound with 10% palladium on carbon as in (i) above.

R. F. Heck, in *Pure and Applied Chemistry*, Vol. 50, pp. 691-701, (1978), has described a new vinylic substitution reaction.

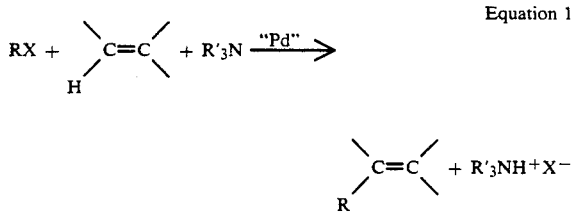

Equation 1

According to the Heck article, the reaction occurs in the presence of a "palladium" catalyst. Such catalyst comprises, usually, a complex of a palladium (II) salt and a phosphine ligand. Heck has shown the reaction of aromatic bromides with various unsaturated alcohols and esters. He states, however, that α, β-unsaturated ketones and aldehydes are polymerized under the reaction conditions.

Others have more recently studied the vinylic substitution reaction. Among these are A. J. Chalk and S. A. Magennis in *Journal of Organic Chemistry*, Vol. 41, pp. 273-278 and 1206-1209 (1976); and J. B. Melpolder and Heck, *Journal of Organic Chemistry*, Vol. 41, pp. 265-272 (1976). S. Cacchi and G. Palmieri in *Synthesis*, July, 1984, pp. 575-577, report the palladium catalyzed synthesis of a disubstituted α, β-unsaturated carbonyl compounds with aryl iodides. S. Cacchi and A. Arcadi have written extensively on the reaction in an article in *Journal of Organic Chemistry*, Vol. 48, pp. 4236-4240 (1983).

SUMMARY OF THE INVENTION

This invention is concerned with a new method for the manufacture of 4-(6'-methoxy-2'-naphthyl)-3-buten-2-one. Contrary to the statement of Heck in *Pure and Applied Chemistry*, Vol. 50, pp. 695 at the fourth line above Table III, that α,β-unsaturated ketones and aldehydes do not undergo the vinylic substitution reaction with aryl bromides using palladium catalyst, it has now been found that 2-bromo-6-methoxynaphthalene reacts quantitatively with methyl vinyl ketone to form the desired compound.

The reaction can best be expressed by the chemical reaction sequence

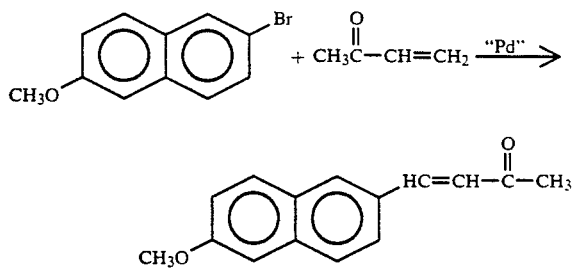

The reaction is carried out in the presence of an inert gas at from about 50° C. to about 200° C. for from about 0.25 to about 10 hours, preferably about 1-3 hours. Preferably the reaction is carried out in a liquid medium which acts as a solvent for the reactants and the catalyst.

Nabumetone is manufactured from the 4-(6'-methoxy-2'-naphthyl)-3-buten-2-one by hydrogenation with, for example, hydrogen in contact with palladium on carbon according to the prior art.

DETAILED DESCRIPTION OF THE INVENTION

As previously stated, the prior art has shown that allyl alcohols and esters containing at least one terminal vinylic hydrogen will undergo the vinyl substitution reaction with aryl bromides and iodides. Conjugated allyl ketones also undergo a similar mono-substitution reaction with aryl iodide in 20-61% yield according to Cacchi and Arcadi, loc cit.; and in 4-7% yield (with the predominant product being a disubstituted moiety) according to Cacchi, loc cit.

Heck (loc cit.) states that α,β-unsaturated aldehydes and ketones do not undergo the reaction but are polymerized under the reaction conditions.

By the present invention, methyl vinyl ketone can also be caused to undergo the substitution reaction in nearly quantitative yields when reacted with 2-bromo-6-methoxynaphthalene.

By an analogous method, 2-bromo-6-hydroxynaphthalene can be reacted with methyl vinyl ketone to form 4-(6'-hydroxy-2'-naphthyl)-3-buten-2-one which can then be methylated to form the compound manufactured by the method of this invention.

According to the invention, 2-bromo-6-methoxynaphthalene is contacted with at least one molar equivalent of methyl vinyl ketone in the presence of a palladium catalyst. The reaction mixture is held at a temperature of from about 50° C. to about 200° C., preferably at from about 75° C. to about 150° C. and, most preferably from about 120° C. to about 150° C. for a time sufficient to cause substantially complete reaction to occur. Typically the reaction time is from about 0.25 to about 10 hours, preferably from about 1 to about 2 hours.

The reaction can be carried out without a solvent or in an inert liquid solvent.

Typical solvents for the reaction can include nitriles, amides, ethers, such materials as:

N-methyl pyrrolidone,
acetonitrile,
dimethyl sulfoxide,
dimethyl formamide,
dimethyl acetamide,
tetrahydrofuran, and the like.

The reaction is carried out in an inert atmosphere to avoid oxidation and by-product formation. Typically a nitrogen, argon, or helium atmosphere is used for the reaction.

The catalyst for the reaction consists essentially of a palladium compound preferably complexed with at least one ligand of the class consisting of trivalent phosphorus compounds. Some palladium catalysts which may be used wherein the palladium is complexed with an appropriate ligand are as follows: bis(triphenylphosphine)dichloro complex, bis(tributylphosphine)dichloro complex, bis(tricyclohexylphosphine)dichloro complex, diallyltriphenylphosphinedichloro complex, triphenylphosphinepiperidinedichloro complex, bis(cyclohexyloxime)dichloro complex, 1,5,9-cyclododecatrienedichloro complex, bis(triphenylphosphine)dicarbonyl complex, bis(triphenylphosphine)diacetate complex, bis(triphenylphosphine)dinitrate complex, bis(triphenylphosphine)sulfate complex, 2,4-pentanedionepalladium (II) complex, tetrakis(triphenylphosphine) complex, and complexes in which some of the ligands are carbon monoxide such as chlorocarbonylbis(triphenylphosphine) complex, and the like, all complexes of palladium.

Some palladium catalysts which may be used for the reaction of the present invention which do not incorporate the phosphine ligand include, for example:

$Pd(NO_3)_2$
$PdCl_2$
$Pd(OCOCH_3)_2$
$PdBr_2$
$PdSO_4$ and the like.

The reactants, methyl vinyl ketone and 2-bromo-6-methoxynaphthalene, can be mixed in equimolar quantities or one of the reactants can be used in excess. Preferably, a slight excess, typically a 5 to 25 wt. % excess, most preferably a 5 to 10 wt. % excess of the methyl vinyl ketone is used to drive the reaction to completion.

An equimolar quantity of the palladium catalyst may be used or, preferably, a lesser amount may be used in the presence of a compound which will regenerate the active catalyst during the reaction. Typically, from about 0.01 to about 0.1 molar amount of catalyst per mole of reactant is used.

Regeneration of the catalyst during reaction is accomplished by addition of an excess of base. As used in this description, a base is a compound which reacts with the hydrogen bromide formed in the reaction regenerating the catalyst and causing formation of an inert material. Base compounds useful for the present invention include, for example:

$NaHCO_3$
$Na_2CO_3$
$KHCO_3$
$K_2CO_3$
$(CH_3)N$
$(C_2H_5)_3N$ and the like

The preferable base for use in this reaction is $NaHCO_3$.

This compound is reasonable in cost and reacts with the hydrogen bromide to form carbon dioxide, water, and the active catalyst. The carbon dioxide and water are inert and are easily separable from the reaction solution on isolation of the product.

The product, 4-(6'-methoxy-2'-naphthyl)-3-buten-2-one is isolated from the reaction mixture by methods well known in the art. Typically, the reaction mixture is poured into water at which time the product is separated as a crystalline solid. The solid is recrystallized to give a pure crystalline material melting at about 121° to 122° C.

EXAMPLE 1

A mixture of 5.92 g of 2-bromo-6-methoxynaphthalene, 2.62 g of methyl vinyl ketone, 0.32 g of dichlorobis(triphenylphosphine)palladium (II), and 2.5 g of $NaHCO_3$ dissolved in 70 mL of N-methylpyrrolidone was charged into a Hastelloy C high pressure autoclave. The autoclave was then charged with nitrogen to a pressure of 25 psig and heated to 140° C. for 5 hours. At the end of the heating cycle, the autoclave was cooled, depressurized, opened, and the contents filtered to remove the solids. Water was added to the filtrate causing a crystalline precipitate to appear. The precipitate was removed by filtration and dried to yield the desired product. The product weighed 4.8 g.

EXAMPLE 2

Example 1 was repeated using only 2.1 g of methyl vinyl ketone and heating the autoclave to 130° C. for 3 hours. The yield was 5.3 g. A portion of the product was recrystallized from ethanol to yield a white solid melting at 120°-121° C. Analysis of the product demonstrated it to be identical to the compound reported in U.S. Pat. No. 4,061,779, Example 20.

What is claimed is:

1. A method of manufacture of 4-(6'-methoxy-2'-naphthyl)-3-buten-2-one which comprises contacting 2-bromo-6-methoxynaphthalene with methyl vinyl ketone in the presence of a palladium (II) catalyst at a temperature of from about 50° C. to about 200° C. for a time sufficient to cause substantially complete reaction to occur.

2. The method of claim 1 wherein the 2-bromo-6-methoxynaphthalene and methyl vinyl ketone are contacted in a liquid solvent for the reactants and the catalysts.

3. The method of claim 1 wherein the reaction time is from about 0.25 hour to about 10 hours.

4. The method of claim 2 wherein the reaction time is from about 0.25 to about 10 hours.

5. The method of claim 4 wherein the temperature of the reaction is from about 120° C. to about 150° C.

6. The method of claim 5 wherein the palladium catalyst is dichlorobis(triphenylphosphine)palladium (II).

7. The method of claim 1 in which the 4-(6'-methoxy-2'-naphthyl)-3-buten-2-one is hydrogenated in the presence of palladium on carbon catalyst to form nabumetone.

8. A method of manufacture of 4-(6,-methoxy-2'-naphthyl)butan-2-one (nabumetone) which comprises contacting 2-bromo-6-methoxynaphthalene with methyl vinyl ketone in the presence of a palladium (II) catalyst at a temperature of from about 50° C. to about 200° C. for a time sufficient to cause substantially complete reaction to occur and then hydrogenating the resultant 4-(6'-methoxy-2'-naphthyl)-3-buten-2-one with hydrogen in contact with palladium on carbon.

* * * * *